(12) United States Patent
Hansen et al.

(10) Patent No.: US 6,988,887 B2
(45) Date of Patent: Jan. 24, 2006

(54) ORTHODONTIC SEPARATORS

(75) Inventors: James D. Hansen, Pasadena, CA (US);
Tsi-Zong Tzou, Arcadia, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 10/078,970

(22) Filed: Feb. 18, 2002

(65) Prior Publication Data

US 2003/0157454 A1    Aug. 21, 2003

(51) Int. Cl.
*A61C 7/00*    (2006.01)
(52) U.S. Cl. .......................................... 433/18; 433/148
(58) Field of Classification Search ................ 433/18, 433/24, 7, 148, 149, 150
See application file for complete search history.

(56) References Cited

U.S. PATENT DOCUMENTS

| | | |
|---|---|---|
| 2,867,905 A | 1/1959 | Meacham |
| 3,488,419 A | 1/1970 | McCune et al. |
| 3,530,583 A | 9/1970 | Klein et al. |
| 3,913,228 A | 10/1975 | Wailshein |
| 4,038,753 A | 8/1977 | Klein |
| 4,054,997 A | 10/1977 | Wallshein |
| 4,412,820 A | 11/1983 | Brummond et al. |
| 4,469,477 A | 9/1984 | Potter |
| 4,565,722 A | 1/1986 | Highgate et al. |
| 4,818,225 A | 4/1989 | Fasnacht |
| 4,933,418 A | 6/1990 | Sterrett |
| 4,946,385 A | 8/1990 | Eckert et al. |
| 4,946,387 A | 8/1990 | Adell |
| 4,950,158 A | 8/1990 | Barngrover et al. |
| 5,068,107 A | 11/1991 | Hollibush et al. |
| 5,145,935 A | 9/1992 | Hayashi |
| 5,378,146 A | 1/1995 | Sterrett |
| 5,399,088 A | 3/1995 | Mechley |
| 5,421,725 A * | 6/1995 | von Weissenfluh ......... 433/149 |
| 5,461,133 A | 10/1995 | Hammar et al. |
| 5,506,300 A | 4/1996 | Ward et al. |
| 5,527,181 A * | 6/1996 | Rawls et al. ................ 433/149 |

(Continued)

FOREIGN PATENT DOCUMENTS

| | | |
|---|---|---|
| EP | 0 594 535 | 4/1994 |
| EP | 0 668 060 | 8/1995 |
| EP | 0 860 149 | 8/1998 |

OTHER PUBLICATIONS

Kirk-Othmer, Encyclopedia of Chemical Technology, Third Edition, vol. 23 "Urethane Polymers", 1983 pp. 576, 577, 584, 585, 587.

(Continued)

*Primary Examiner*—Melba N. Bumgarner
(74) *Attorney, Agent, or Firm*—James D. Christoff (57) ABSTRACT

An orthodontic separator, dimensioned such that it can be inserted between adjacent teeth. The separator is characterized in that it exhibits an increase in compressive force after insertion between adjacent teeth in the oral environment. The separator, after insertion, exerts sufficient force on the adjacent teeth to push the teeth apart.

23 Claims, 5 Drawing Sheets

U.S. PATENT DOCUMENTS

| | | | |
|---|---|---|---|
| 5,573,400 A * | 11/1996 | Asher | 433/136 |
| 5,665,822 A | 9/1997 | Bitler et al. | |
| 5,876,208 A | 3/1999 | Mitra et al. | |
| 5,993,972 A | 11/1999 | Reich et al. | |
| 6,169,084 B1 | 1/2001 | Bunnell et al. | |
| 6,203,317 B1 | 3/2001 | Davanathan | |
| 6,280,186 B1 | 8/2001 | Logan | |
| 6,388,043 B1 * | 5/2002 | Langer et al. | 528/80 |
| 2001/0049081 A1 | 12/2001 | Krupp | |

OTHER PUBLICATIONS

Biomedical Elastomers, Elastomers in Biomedical Applications: an Overview of Types and End-Uses, McMillin, Nov. 1988, pp. 22-27.

"Thermoplastic Elastomers" A Comprehensive Review, Legge et al., 1987, Chapters 2, 5 & 7.

Polyurethanes in Medicine, Lelah et al., CRC Press, Inc. Boca Raton, Florida, pp. 27-30.

* cited by examiner

ORTHODONTIC SEPARATORS

BACKGROUND OF THE INVENTION

1. Field of the Invention

This invention relates to separating teeth.

2. Description of the Related Art

Orthodontic treatment generally involves application of mechanical forces to urge improperly positioned teeth into correct alignment. One common form of orthodontic treatment includes the use of elastomeric separators to increase the space between teeth before fitting orthodontic bands. The materials used for elastomeric separators are typically hydrophobic polyurethanes. During insertion of an elastomeric separator, the separator is stretched and inserted between adjacent teeth using a sawing action. Tools that may be used to stretch and insert separators include dental floss and pliers.

Inserting separators is often difficult, especially when the space between the adjacent teeth is small. Once inserted between adjacent teeth, the separator is under compression and generates a force to separate the adjacent teeth. Currently, separator products start out separating teeth quickly and lose effect within about a day. This effect can be due to a combination of decay in compressive force, resulting from relaxation of the separator, and the increasing gap between the adjacent teeth. An additional problem occurs when the teeth move apart and the separator becomes lost in the mouth.

SUMMARY OF THE INVENTION

In general, the invention features an orthodontic separator that can be used to separate a pair of adjacent teeth in a patient's mouth. The invention also features a method for separating adjacent teeth using the separator.

More particularly, the present invention is directed in one aspect to an orthodontic separator. The separator is dimensioned such that it can be inserted between adjacent teeth. The separator is characterized in that when inserted between adjacent teeth in the oral environment, it exhibits an increase in compressive force, and the separator exerts sufficient force on the adjacent teeth to push the teeth apart.

The orthodontic separator is dimensioned to allow for insertion between the adjacent teeth. Prior to insertion, the orthodontic separator is characterized as having a volume, $V_0$, in the absence of an applied force. Once the orthodontic separator is positioned between the adjacent teeth in the patient's mouth, the orthodontic separator begins to expand to a volume $V_1$, where $V_1 > V_0$. The expansion causes the orthodontic separator to exhibit an increase in compression force, thereby exerting sufficient force on the adjacent teeth to push the teeth apart.

The orthodontic separator can be designed to expand isotropically or anisotropically. It can also continue to expand over time, exerting a compressive force on the adjacent teeth despite the widening gap between the teeth and decay in compressive force resulting from relaxation of the separator. In addition, it can provide satisfactory resistance to force degradation over extended periods of time (e.g., the amount of time the separator is used in the patient's mouth).

The separator can be switched between an expanded configuration, where the separator will remain in place between the teeth, and a contracted configuration, where the separator can be readily inserted or removed from between the teeth. This is a particularly useful advantage because it allows the separator to be temporarily reconfigured and removed for any purpose and then repositioned between the teeth to continue the treatment.

Optionally, the separators may be molded from a polymeric material, and multiple separators may be provided on a single sprue for the convenience of the orthodontist. In addition, the separator may be included as part of an orthodontic kit that contains, for example, orthodontic brackets, bands, arch wires, ligatures, and the like.

The details of one or more embodiments of the invention are set forth in the accompanying drawings and the description below. Other features, objects, and advantages of the invention will be apparent from the description and drawings, and from the claims.

DETAILED DESCRIPTION OF THE PREFERRED EMBODIMENTS

Figure 1A:
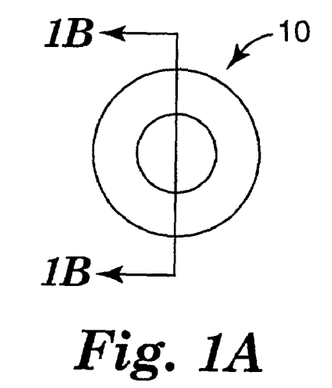
FIG. 1A is a top view of an O-ring shaped orthodontic separator according to one embodiment of the invention.
Figure 1B:
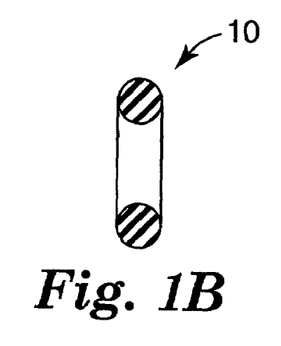
FIG. 1B is a side cross-sectional view of the separator shown in FIG. 1A, taken along lines 1B—1B of FIG. 1A.
Figure 1C:
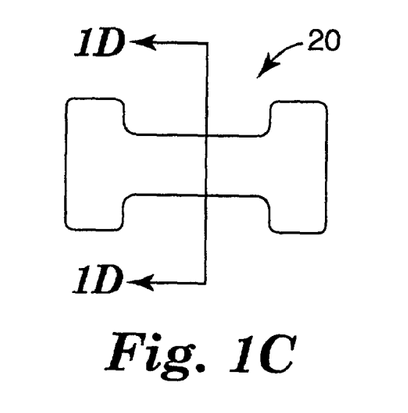
FIG. 1C is a top view of a dog bone shaped orthodontic separator according to another embodiment of the invention.
Figure 1D:
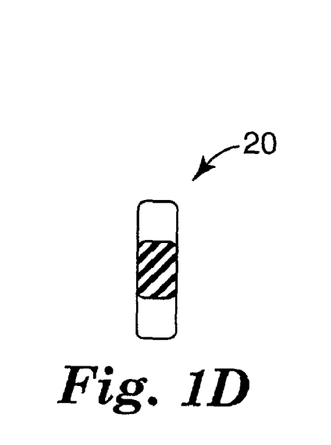
FIG 1D is a side cross-sectional view of the separator shown in FIG. 1C, taken along lines 1D—1D of FIG. 1C.

The orthodontic separator is prepared in a shape having dimensions such that it may be readily inserted between adjacent teeth in a patient's mouth. Examples of useful shapes include o-rings, slabs, coils, and dog bones. Preferred shapes include O-rings such as the O-ring separator 10 shown in FIGS. 1A and 1B and dog bones such as the dog bone separator 20 shown in FIGS. 1C and 1D.

Useful materials for the orthodontic separator are water or heat activated when placed between adjacent teeth in a patient's mouth and exert a force sufficient to separate the teeth. One class of materials suitable for this purpose includes hydrophilic materials that expand upon absorption of water or saliva found in the patient's mouth. Examples of orthodontic separators made of such hydrophilic materials include the separator 10 shown in FIGS. 1A and 1B and the separator 20 shown in FIGS. 1C and 1D.

A convenient measure of hydrophilicity is the amount of water absorbed by the material, as determined, for example, according to the procedure described in ASTM D570. Preferred hydrophilic materials absorb between about 6% and about 120% by weight water, and undergo a volume increase of between about 80% to about 100%, after immersion in water for 2 hours. Particularly preferred hydrophilic materials absorb water rapidly in the first 2 hours and more slowly afterwards. For example, particularly preferred hydrophilic materials undergo a weight increase of between about 50 to about 70% after immersion in water for 1 hour at about 37° C., and about 60 to about 80% weight increase after immersion in water for 16 hours at 37° C.

Examples of useful hydrophilic materials include hydrophilic polymers such as polyurethanes, polyalkylene oxide polymers and copolymers (e.g., ethylene oxide copolymers, polyethylene glycols, polymethylene glycols, polytrimethylene glycols, polyoxyethylene-polyoxypropylene block copolymers, and the like), polyvinylpyrrolidones, cellulosic polymers (e.g., carboxymethylcellulosic polymers), polyamides, polyacrylamides, polyether-polyamide copolymers, ethylene vinyl acetate copolymers, polyvinyl alcohol (e.g., in the form of a hydrophilic sponge available commercially from Hydrofera LLC, Willimantic, Conn. under the trade designation SAUFERA), polyvinyl acetate, and polymethylmethacrylate, and derivatives thereof. These polymers may be used alone or in combination with each other. Polyurethanes are particularly useful hydrophilic polymers for the orthodontic separator. Suitable polyurethanes are prepared by reaction of a polyisocyanate (e.g., an aliphatic diisocyanate such as hexamethylene diisocyanate or isophorone diisocyanate) with a polyester, polyether, or polycarbonate polyol, with polyether polyols being preferred. For example, the polyurethane may be an aliphatic polyether polyurethane in the form of a segmented block copolymer having a plurality of oxyethylene units that impart hydrophilicity to the polymer. Such aliphatic polyether polyurethanes are available commercially from Thermedics Polymer Products, Woburn, Mass. under the trade designation TECOPHILIC.

A second class of useful materials for the orthodontic separator includes shape memory materials, such as shape memory metal alloys and shape memory polymers. Such materials are inserted between a patient's teeth, and heat activated upon exposure to the higher temperatures encountered in the patient's mouth to exert a force on the teeth that causes the teeth to separate. An example of an orthodontic separator made of a shape memory material is the coil separator 30 illustrated in FIGS. 2 and 3.

Figure 2:
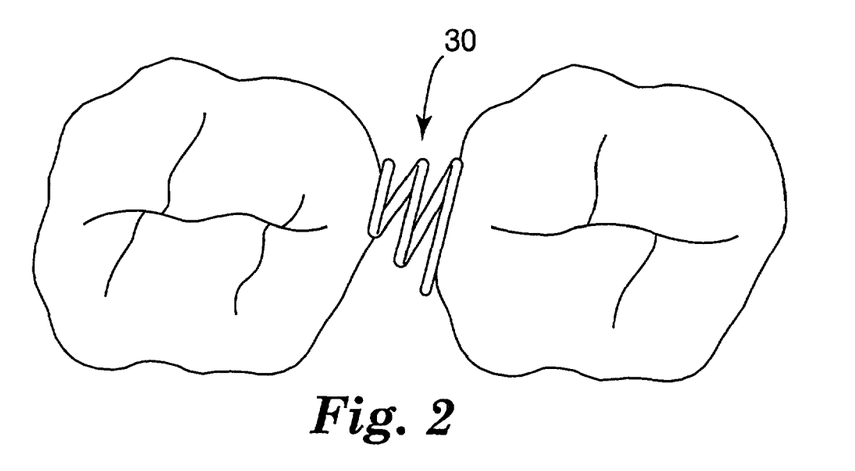
FIG. 2 shows a top view of two adjacent teeth separated by an orthodontic separator.
Figure 3:
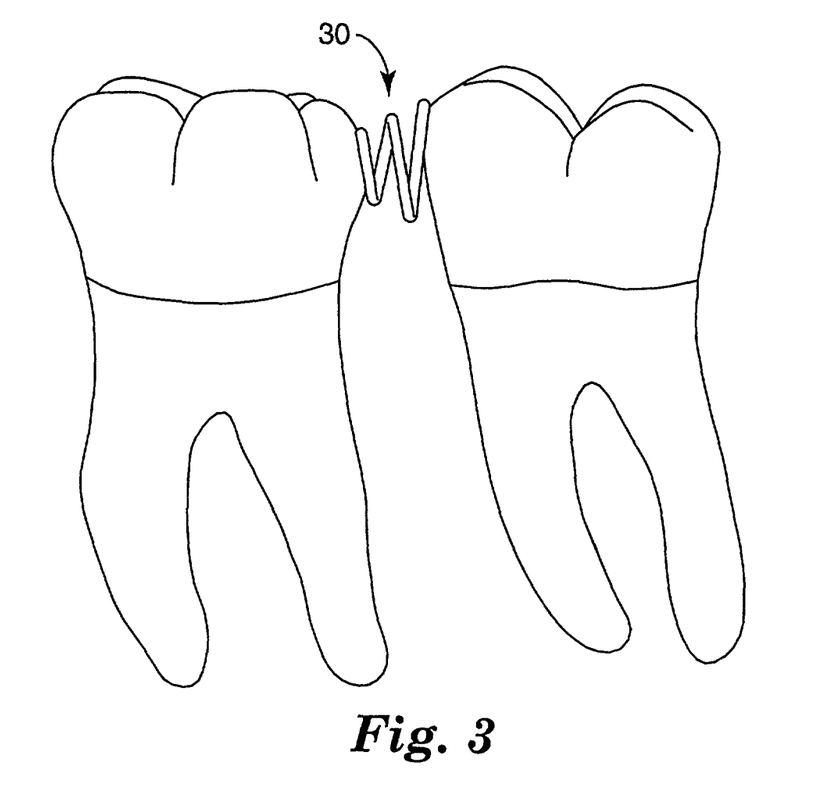
FIG. 3 shows a perspective view of two adjacent teeth separated by an orthodontic separator.

Preferably, the coil separator 30 has an overall helical configuration so that adjacent sections of the coil nest within each other when the coil is collapsed. In this manner, the coil can be compressed to a relatively compact configuration, a particular advantage when attempting to insert the coil between teeth that are closely adjacent to one another. However, other shapes are also possible, such as coil springs having an overall cylindrical configuration.

Additionally, orthodontic separators made of shape memory materials may have configurations other than coiled configurations. For example, the separator may have a shape similar to a washer spring having a domed configuration in cross-sectional view, such as a "Belleville" spring. Other shapes are also possible, such as shapes similar to finger washers and wave washers.

Shape memory metal alloys suitable for the making the orthodontic separator of the present invention include those composed substantially of nickel and titanium (NiTi) or alloys of other metals known to exhibit shape memory effects (e.g., CuZnAl, CuAlNi, FeNiAl, and InTi). Elements such as boron, cerium, cobalt, iron, copper, vanadium, and zirconium may also be added to tailor the mechanical properties to the intended application. An example of a suitable shape memory alloy is nitinol (NiTi), which is commercially available from NDC, Fremont, Calif.

Useful shape memory polymers include segmented linear polyurethanes having hard segments and a soft segments. The hard segments are typically crystalline, with a defined melting point, and the soft segments are typically amorphous, with a defined glass transition temperature. Suitable polymers used to prepare the hard and soft segments include various polyethers, polyacrylates, polyamides, polysiloxanes, polyurethanes, polyether amides, polyurethane/ureas, polyether esters, urethane/butadiene copolymers, and polyesters. Examples of shape memory polymers are described in Langer et al., U.S. Pat. No. 6,169,084, Hayashi et al., U.S. Pat. No. 5,145,935, Bitler et al., U.S. Pat. No. 5,665,822, and Ward et al., U.S. Pat. No. 5,506,300.

The materials for the orthodontic separator can contain conventional adjuvants such as chemical or photochemical polymerization initiation systems, accelerators, inhibitors, stabilizers, radio-opaque additives (e.g., barium sulfate), viscosity modifiers (including waxes, extending oils, and elastomeric gums), toughening agents (e.g., polypropylene), fibers, surfactants, antioxidants, extending or reinforcing fillers (e.g., fumed silica or zinc oxide), flavorants (both natural and synthetic, such as peppermint oil, menthol, and sweeteners), colorants (e.g., dyes or pigments), preservatives, antioxidants and antimicrobial agents (e.g., hydroquinone, butylated hydroxytoluene, ascorbic acid, p-hydroxybenzoic acid, alkyl esters, sodium sorbate, and thymol), anti-plaque additives (e.g., organophosphonates, triclosan and others such as those disclosed in U.S. Pat. No. 3,488,419), and oral therapeutic agents (e.g., fluoride salts, chlorhexidine, and allantoin). Lyophilic polymer additives, such as starch, natural gums, poly(vinyl alcohol), gelatin, and the like may also be included. The amounts of such ingredients are selected to achieve a desired effect without compromising the ability of the material to expand upon insertion between a patient's teeth to exert sufficient force to separate the teeth.

The orthodontic separator may also include an outer coating that can serve a variety of purposes, such as to improve slip to ease insertion and removal of the separator between the adjacent teeth, and to reduce adhesion of bacteria and proteinaceous substances to the surfaces of the orthodontic separator. The coating may be provided as a continuous or semi-continuous layer. Suitable coatings to reduce adhesion of bacteria and proteinaceous substances are described by Mitra, et al. in U.S. Pat. No. 5,876,208 and include ethylenically unsaturated compounds such as 2,2-bis[4-(2-hydroxy-3-methacryloxypropoxy)phenyl]propane (BIS-GMA) and 2-hydroxyethyl methacrylate (HEMA). Surfactants may be incorporated at very small amounts in the coating composition, and may be either non-ionic or ionic surfactants. Coatings to enhance slip, and thereby ease insertion of the separator between the adjacent teeth, can be prepared from compositions including amphiphilic polyether polyurethanes (e.g., as described by Reich et al. in U.S. Pat. No. 5,993,972).

The orthodontic separator may be made by a variety of conventional polymer processing techniques, including, for example, extrusion, injection molding, liquid injection molding, compression molding, reaction injection molding, pressing, drawing, and die cutting. Orthodontic separators made from shape memory metal alloy materials, such as NiTi metal alloy, can be shaped by bending, twisting, or squeezing, and made to retain their new shape using a combination of mechanical and thermal "training." The training process involves heating the deformed part to about 400° C., and quickly cooling it in a water bath or by rapid air cooling, thus freezing the material's crystalline structure in a new position. Due to the energetics of the crystal structure, the separator is unable to resume its original shape unless external heat is applied. The shape of the shape memory separator may be pre-programmed or trained such that the separator will forcefully return to its pre-programmed shape when heated from below to above the transformation temperature range.

In use, the orthodontic separator is inserted between two adjacent teeth in a patient's mouth and allowed to be activated by water or heat. Upon activation(and as shown in the exemplary illustrations FIG. 2 and FIG. 3) the orthodontic separator exerts sufficient force on the adjacent teeth to push the teeth apart. The force exerted by the orthodontic separator is the sum of the initial compressive force exerted on the adjacent teeth when first inserted and the additional compressive force provided by expansion or heat activation of the material. Once the teeth have been pushed apart, other orthodontic devices (e.g., bands, arch wires, brackets, ligatures, and the like) may be fitted onto the patient's teeth.

In the case of hydrophilic materials, which expand when they absorb water present in the patient's mouth, additional sources of water may be used to initiate and/or accelerate expansion of the orthodontic separator. For example, a spray unit can be used to spray water on the separator after placement between the patient's teeth. The hydrophilic orthodontic separators exhibit a force increase of greater than about 5% within about 4 hours when measured by the Compressive Force Measurement Test Procedure, described below. Similarly, in the case of shape memory materials, which are activated upon encountering the elevated temperatures found in the patient's mouth (about 37° C.), additional thermal stimuli may be used to initiate and/or accelerate expansion. Examples of sources of thermal stimuli include infrared, microwave, resistive heating, and radio frequency heat sources.

The separator can be switched between an expanded or activated configuration, where the separator will remain in place between the teeth, and a contracted or unactivated configuration, where the separator can be readily inserted or removed from between the teeth. The orthodontic separators may be switched to a contracted or unactivated configuration and removed from a patient's mouth after use by a variety of methods, such as, for example, by hand instruments, drying (e.g., using an air syringe), or cooling with a compressed coolant gas (e.g., $N_2$ or ENDO-ICE Refrigerant Spray available from Coltene-Whaledent, Inc. of Mahway, N.J.)

EXAMPLES

Compressive Force Measurement Test Procedure

Figure 4A:
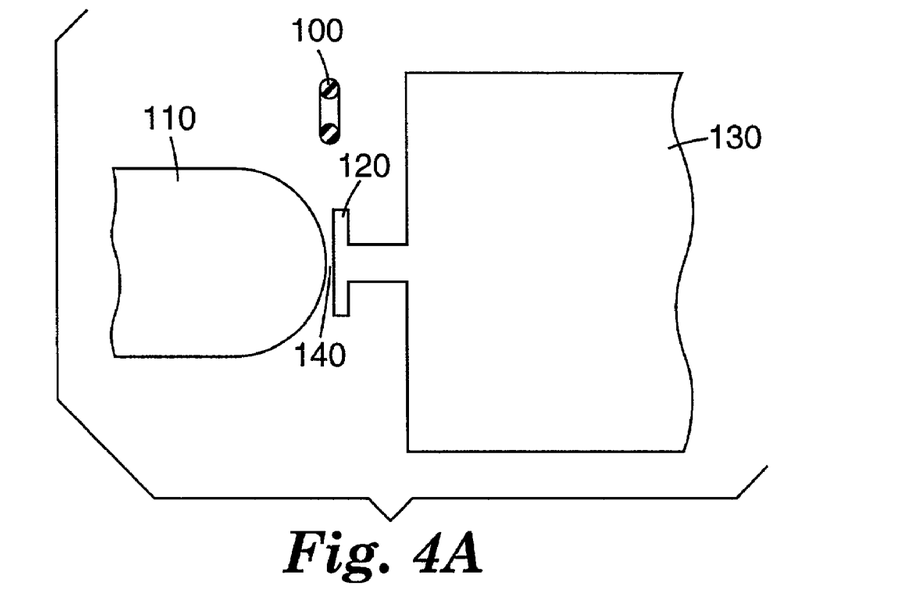
FIG. 4 shows a test apparatus for compressive force measurements.
Figure 4B:
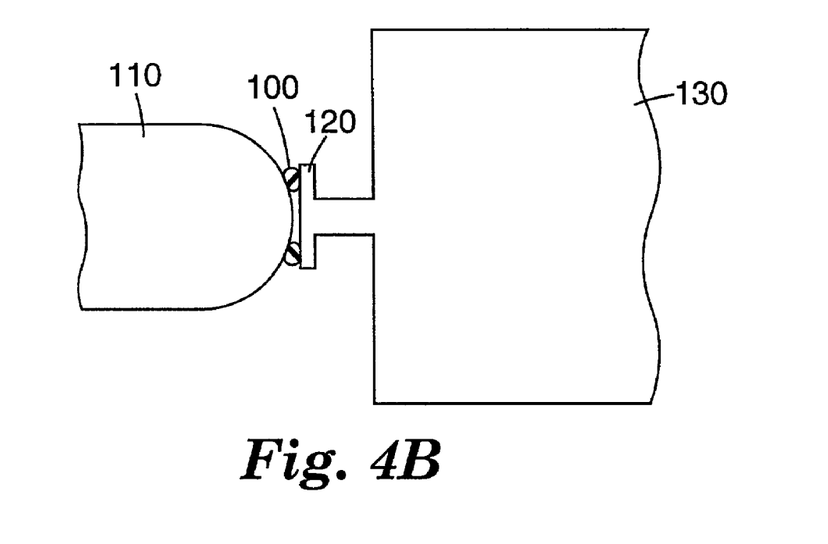

Compression force measurements were recorded in duplicate for each separator using the apparatus depicted in FIG. 4A. Referring to FIG. 4A, the apparatus consisted of a hemisphere-shaped fixed mass 110 measuring 0.5 inch in diameter and a plate 120. The plate 120 was attached to a force transducer 130 (Model DFG 10 Chatillon force gauge available from John Chatillon & Sons Inc., New York, N.Y.). The gap 140 between the fixed mass 110 and the plate 120 was held constant at about 20 mil during the measurement process. The separator 100 was stretched using dental floss and inserted between the hemisphere 110 and the plate 120. FIG. 4B illustrates the force measurement apparatus after insertion of the separator into gap 140. At time zero, water was squirted onto the separator to initiate expansion. The compressive force generated by the expanding separator was recorded over time by the Chatillon force gauge.

Example 1

Figure 5:
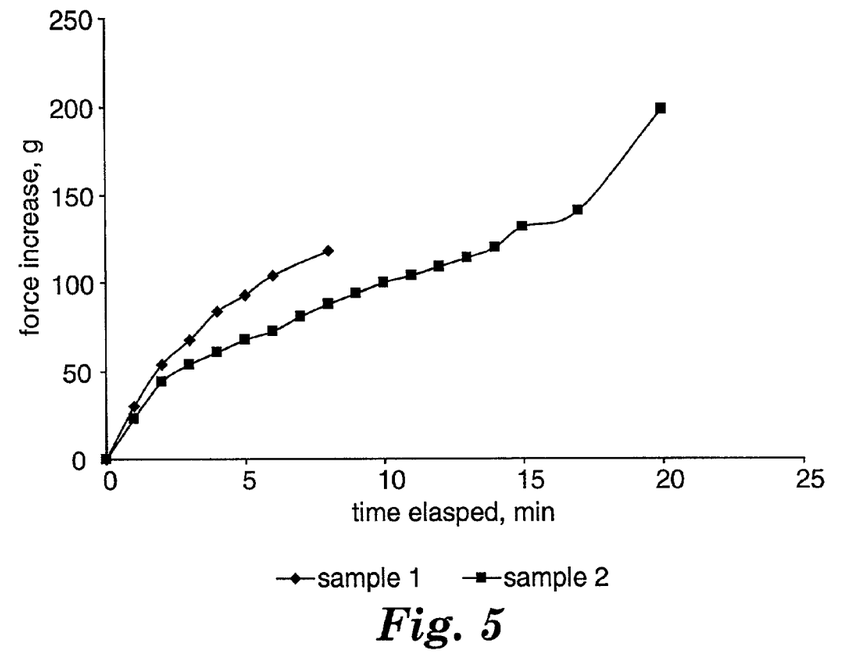
FIG. 5 shows the compressive force increase of tubing samples made of TECOPHILIC HP-93A-100-B20 upon absorbing water.

Compressive force measurements were recorded for tubing samples made of TECOPHILIC HP-93A-100-B20 using the compressive force measurement test procedure with the exception that the gap distance was set slightly less than the tubing length to hold the tubing in place after insertion. The samples tested had an inner diameter of 0.050", an outer diameter of 0.074" and a length of 0.138." The initial compressive forces for the two samples were 40 g and 100 g for samples 1 and 2, respectively. FIG. 5 plots the increase in compressive force over time for the two samples. Within 10 minutes, the force increase for samples 1 and 2 was about 100 g. By 20 minutes, the force increase for sample 2 was about 200 g.

Example 2

Two sets of separators were injection molded into an O-ring shape with an inner diameter of 0.085 inches, an outer diameter of 0.175 inches, and a thickness of 0.045 inches. One set contained no barium sulfate, and one set contained 20 wt % barium sulfate. Two radio-opaque control samples (Control A and Control B) were commercially available SX separators (3M Unitek 406-086, Monrovia, Calif.) with an inner diameter of 0.090 inches, an outer diameter of 0.190 inches, and a thickness of 0.050 inches The control samples contained 20 wt % barium sulfate.

Figure 6:
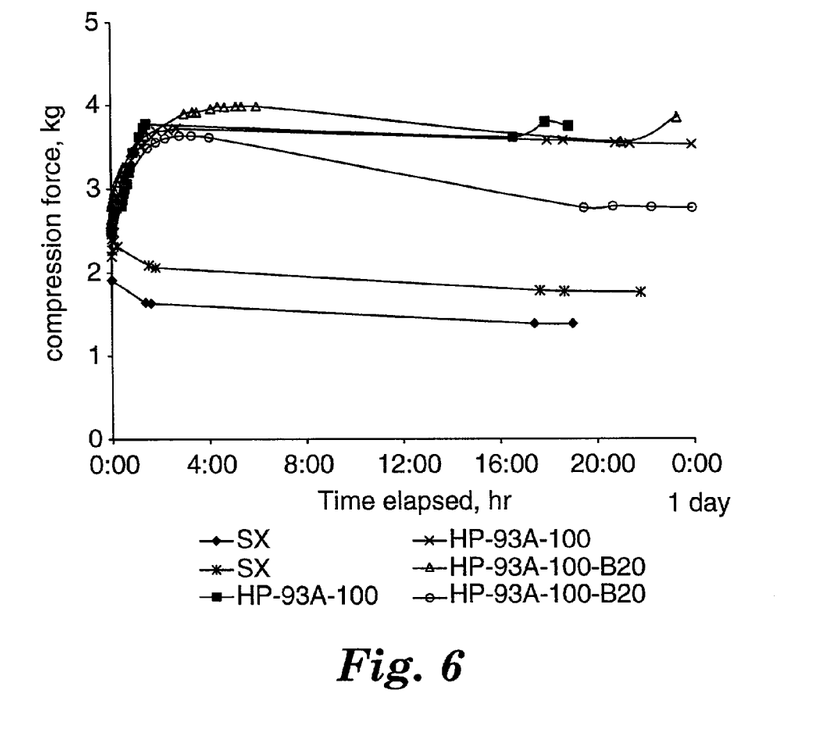
FIG. 6 shows the compressive force increase of commercially available SX orthodontic separators and separators made of TECOPHILIC HP-93A-100 and TECOPHILIC HP-93A-100-B20 upon absorbing water.

Compressive force measurements were recorded for the three sets of separators using the compressive force measurement test procedure. FIG. 6 plots compressive force over time for each of the three sets of separators. The results from these measurements at time zero and after 1.5 hours are given in Table 1. Upon absorbing water, the separators made from the HP-93A-100 TECOPHILIC material (both with and without barium sulfate) exhibited an increase in compressive force. In contrast, the control separators showed a continuous decrease in compressive force over time.

TABLE 1

|  | Control | | HP-93A-100 | | HP-93A-100-B20 | |
| --- | --- | --- | --- | --- | --- | --- |
|  | Sample A | Sample B | Sample 1 | Sample 2 | Sample 1 | Sample 2 |
| Force at 0 hours, kg | 1.91 | 2.46 | 2.5 | 2.2 | 2.8 | 2.6 |
| Force at 1.5 hours, kg | 1.64 | 2.09 | 3.8 | 3.6 | 3.64 | 3.51 |
| Δ Compression Force, kg | −0.27 | −0.37 | +1.3 | +1.4 | +0.84 | +0.91 |

Example 3

Figure 7:
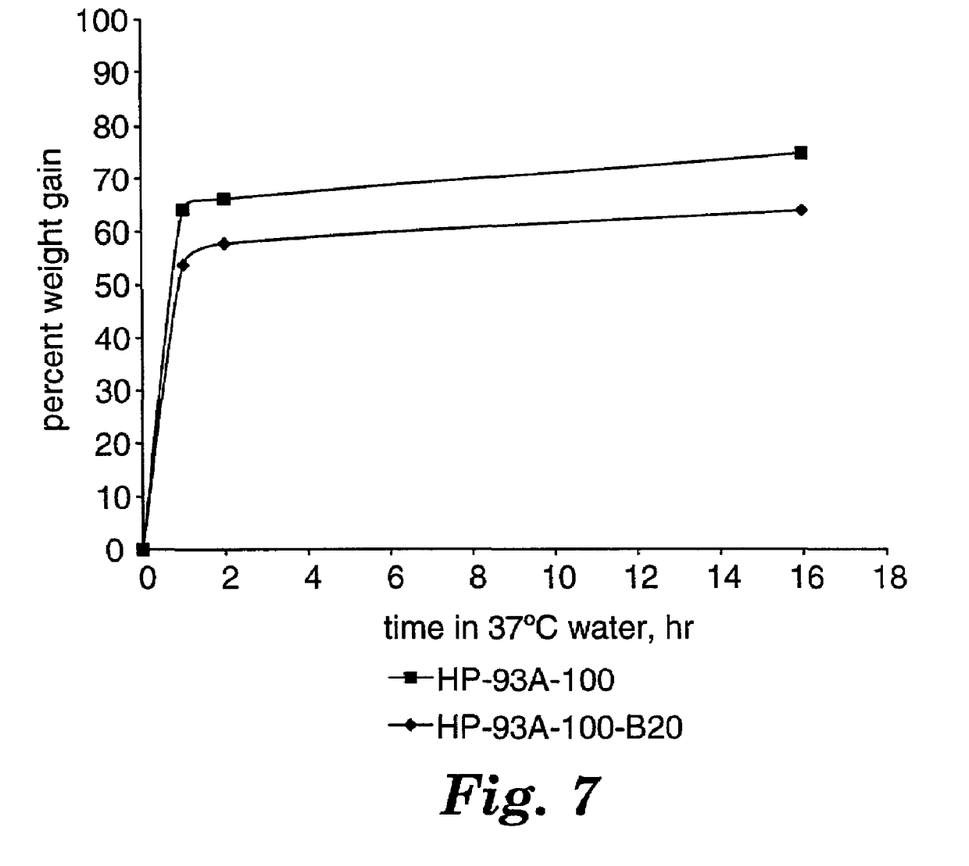
FIG. 7 shows the rate of water absorption of TECOPHILIC HP-93A-100-B20 and TECOPHILIC HP-93A-100 orthodontic separators upon absorbing water.

This example describes the extent and rate of expansion for separators prepared from TECOPHILIC HP-93A-100 with and without barium sulfate. The separators were injection molded according to the procedure described in Example 2. Expansion was characterized by percent weight gain upon water absorption. Percent weight gain was calculated as $(W-W_0)/W_0 \times 100$, where $W_0$ was the initial separator weight (dry), and W was the separator weight at time t (wet). Initial separator weights were taken at atmospheric conditions. Separators were then immersed in 37° C. water. The separators were removed at different time points, blotted dry to remove excess water, and weighed. FIG. 7 shows the percent weight gain over time for the two separators. Water absorption occurred rapidly in the first 2 hours and slowly afterwards. Weight gain reached 75% and 64% for the separators without and with barium sulfate, respectively, after immersion in 37° C. water for 16 hours.

Example 4

This example describes the extent and rate of expansion for separators prepared from TECOPHILIC HP-93A-100 with and without barium sulfate. The separators were molded according to the procedure described in Example 2. Expansion was characterized by an increase in the linear dimensions (ID, OD, and thickness) or volume upon water absorption. Initial (dry) and final (wet) linear dimensions and volumes for the two sets of separators are given in Table 2. Table 2 also gives the % increase in each of the linear dimensions and volumes for the separators with and without barium sulfate. Percent volume increase was calculated as $(V-V_0)/V_0$, where $V_0$ is the initial separator volume, and $V$ is the final separator volume after immersion in water for 2 hours. Similar definitions applied to the increase in ID, OD and thickness.

TABLE 2

| | Material | | | | | |
|---|---|---|---|---|---|---|
| | TECOPHILIC HP-93A-100 | | | TECOPHILIC HP-93A-100-B20 | | |
| | Condition | | | | | |
| | DRY | WET | % increase | DRY | WET | % increase |
| ID, inches | 0.0714 | 0.0880 | 23 | 0.0595 | 0.0686 | 15 |
| OD, inches | 0.1691 | 0.2122 | 26 | 0.1619 | 0.1962 | 21 |
| Thickness, inches | 0.0503 | 0.0630 | 25 | 0.0523 | 0.0643 | 23 |
| Volume, inches$^3$ | 0.00073 | 0.00145 | 99 | 0.00073 | 0.00134 | 83 |

A number of embodiments of the invention have been described. Nevertheless, it will be understood that various modifications may be made without departing from the spirit and scope of the invention. Accordingly, other embodiments are within the scope of the following claims.

What is claimed is:

1. An orthodontic separator having the shape of an o-ring, said separator dimensioned such that it can be inserted between adjacent teeth, and characterized in that when inserted between adjacent teeth in the oral environment and water activated, it exhibits an increase in compressive force on the adjacent teeth sufficient to push the teeth apart, and wherein said separator comprises a hydrophilic polymer.

2. The orthodontic separator according to claim 1, wherein the compressive force exerted by the separator increases by greater than about 5% within about 4 hours as measured by the Compressive Force Measurement Test Procedure.

3. The orthodontic separator according to claim 1, wherein said polymer expands from an original volume $V_0$ to a volume $V_1$ in the oral environment, where $V_1>V_0$.

4. The orthodontic separator according to claim 1, wherein said hydrophilic polymer absorbs between 6 and 120% by weight water.

5. The orthodontic separator according to claim 1, wherein said hydrophilic polymer undergoes a weight increase of between 50 to 70% after immersion in water for 1 hour at 37° C.

6. The orthodontic separator according to claim 1, wherein said hydrophilic polymer undergoes a volume increase of between 80 to 100% after immersion in water for 2 hours.

7. The orthodontic separator according to claim 1, wherein said hydrophilic polymer comprises a polyurethane.

8. The orthodontic separator according to claim 7, wherein said polyurethane comprises an aliphatic polyether polyurethane.

9. The orthodontic separator according to claim 1, wherein said hydrophilic polymer is selected from the group consisting of cellulosic polymers, polyamides, polyether polyamide copolymers, ethylene vinyl acetate copolymers, polyvinyl alcohol, polyvinyl acetate, polymethylmethacrylate, ethylene oxide copolymers, and combinations thereof.

10. The orthodontic separator according to claim 1, wherein said separator comprises a radio-opaque additive.

11. An orthodontic separator, said separator dimensioned such that it can be inserted between adjacent teeth, said separator being characterized in that when inserted between adjacent teeth in the oral environment, it exhibits an increase in compressive force, and wherein said separator comprises a shape memory metal alloy, and wherein said separator is in the shape of a coil or washer.

12. The orthodontic separator according to claim 11, wherein said metal alloy comprises NiTi.

13. The orthodontic separator of claim 11, wherein said separator is in the shape of a coil which has an overall helical configuration, such that adjacent sections of the coil nest within each other when the coil is collapsed.

14. The orthodontic separator of claim 11, wherein said separator is in the shape of a finger washer, wave washer, or domed washer.

15. A method for separating a pair of adjacent teeth in a patient's mouth comprising inserting an orthodontic separator between adjacent teeth, wherein upon insertion said separator is water activated to exert sufficient force on the adjacent teeth to push the teeth apart, said separator having the shape of an o-ring or dog bone, dimensioned such that it can be inserted between adjacent teeth, and characterized in that when inserted between adjacent teeth in the oral environment, it exhibits an increase in compressive force.

16. The method according to claim 15 further comprising removing said separator from between the teeth by drying said separator with an air syringe.

17. A method for separating adjacent teeth in a patient's mouth comprising inserting an orthodontic separator consisting essentially of a shape memory material between the teeth, wherein upon insertion said separator is heat activated to exert sufficient force on the adjacent teeth to push the teeth apart.

18. The method according to claim 17, wherein the force exerted by the separator increases by greater than about 5% within about 4 hours as measured by the Compressive Force Measurement Test Procedure.

19. The method according to claim 17 further comprising removing said separator from between the teeth by applying a compressed coolant gas to said separator.

20. A method of using the separator of claim 11, comprising inserting said separator between adjacent teeth, wherein upon insertion said separator is heat activated to exert sufficient force on the adjacent teeth to push the teeth apart.

21. The method of claim 20, further comprising removing said separator from between the teeth by applying a compressed coolant gas to said separator.

22. A method for separating adjacent teeth in a patient's mouth, comprising inserting an orthodontic separator between adjacent teeth, wherein upon insertion said separator is heat activated to exert sufficient force on the adjacent teeth to push the teeth apart, said separator having the shape of an o-ring or dog bone, dimensioned such that it can be inserted between adjacent teeth, and characterized in that when inserted between adjacent teeth in the oral environment, it exhibits an increase in compressive force.

23. The method of claim 22, further comprising removing said separator from between the teeth by applying a compressed coolant gas to said separator.

* * * * *